(12) United States Patent
Blount

(10) Patent No.: US 6,908,995 B2
(45) Date of Patent: Jun. 21, 2005

(54) PRODUCTION OF CARBOHYDRATES, ALCOHOL AND RESINS FROM BIOMASS

(76) Inventor: David H. Blount, 6728 Del Cerro Blvd., San Diego, CA (US) 92120

( * ) Notice: Subject to any disclaimer, the term of this patent is extended or adjusted under 35 U.S.C. 154(b) by 13 days.

(21) Appl. No.: 09/754,580

(22) Filed: Jan. 5, 2001

(65) Prior Publication Data

US 2004/0121436 A1 Jun. 24, 2004

(51) Int. Cl.$^7$ ............................. C08B 37/00; C12P 7/06
(52) U.S. Cl. ...................... 536/123; 536/1.11; 536/101; 536/124; 435/161
(58) Field of Search .............................. 536/1.11, 101, 536/123, 124; 435/161

(56) References Cited

U.S. PATENT DOCUMENTS 4,321,360 A * 3/1982 Blount ....................... 536/128
4,650,689 A * 3/1987 Hedrick ..................... 426/600
6,608,184 B2 * 8/2003 Blount ....................... 536/1.11

* cited by examiner

Primary Examiner—James O. Wilson
Assistant Examiner—Ganapathy Krishnan

(57) ABSTRACT

Ethanol is produced from biomass by the process of a heated aqueous solution containing 20 to 40 percent alkali metal hydroxide to break the lignin-cellulose bond. Then the biomass is heated further to remove carbon dioxide from the cellulose and lignin to produce a mixture of carbohydrates, modified sodium lignin, micro-cellulose, lignin-cellulose resinous products and sodium carbonate. Water is added to the mixture and most of the mixture is water soluble. An acidic salt forming compound is added to the aqueous solution until a pH of 3–7 is obtained. The lignin is precipitated. The lignin-cellulose resinous products float to the top and is skimmed off. The solution containing the carbohydrates and salt is decanted off the lignin and is concentrated by evaporating off water. The carbohydrates crystalizes from the solution and the water and salt is filtered off. Water is added to the carbohydrates then it is fermented to form ethanol. The ethanol is recovered from the water by evaporation.

3 Claims, No Drawings

PRODUCTION OF CARBOHYDRATES, ALCOHOL AND RESINS FROM BIOMASS

FIELD

The invention concerns Biomass materials being converted to cellulose, lignin, hemi-cellulose, carbohydrates and carbon dioxide by an economical method wherein heat, water and alkali catalyst recoverable and reused. This method consist of mixing the biomass with a recovered aqueous alkali metal hydroxide, then heat the mixture while agitating to evaporated off excess water. The heat is continued until reaction is exothermic, and heat is controlled by means of a heat exchange system. The aqueous alkali metal solution breaks the lignin-cellulose bond. On further heating carbon dioxide is removed from the lignin and cellulose materials thereby producing water soluble materials, consisting of modified sodium lignin, hemi-cellulose, carbohydrates and tall oils, fatty oils and resin oils. Over 90 percent of the biomass is converted to water soluble products and the carbohydrates may be crystalized out from a concentrated aqueous solution of the converted biomass. The carbohydrates are fermented to alcohol.

BACKGROUND OF THE INVENTION

This invention relates to an improved and an economical process to convert biomass containing lignin-cellulose into water soluble hemicellulose, carbohydrates, lignin, lignin-cellulose resinous products, tall oil, turpentine and CO2. In U.S. Pat. No. 4,321,360 issued Mar. 22, 1982 to David H. Blount, M. D., it illustrated the process to break-down cellulose-containing plants into water-soluble polymers, but did not include the production of ethanol, lignin resinous products and the recover of the alkali metal catalyst. Other inventors have utilized acids to break down the cellulose to carbohydrates or may use an alkali metal hydroxide to separate the lignin from cellulose then using an acid such as sulfuric acid to break down the cellulose to carbohydrates. In the improved process of this invention, the biomass is first mixed and wet with the recovered aqueous alkali metal hydroxide in order to distribute the alkali metal catalyst though out the biomass and break the lignin-cellulose bond. The alkali metal hydroxide is used in a sufficient amount to produce a thermal reaction. This reaction removes carbon dioxide from the cellulose to produce carbohydrates and from the lignin to produce a modified lignin. This process also differs from U.S. Pat. No. 4,321,360, because in the process of evaporating off the excess water the lignin-cellulose bond is broken, then when the biomass is further heated the cellulose is converted to carbohydrates by the loss of carbon oxide bonds and carbon dioxide is produced. This method is an improvement because over 90% of the biomass is converted to water soluble material and the yield of carbohydrates is greatly increased over that produced by the method of U.S. Pat. No. 4,321,360. Alcohol and a more chemically active modified lignins are produced, and also heat, water, alkali metal catalyst and alkaline earth metal oxide are recovered for reuse. When the method of this invention is compared to other methods using alkali catalyst, there is a utilization of much less energy for heating the reactants, because the reaction between the dried alkali metal hydroxide and cellulose is exothermic due to the higher ratio of the alkali metal hydroxide to the cellulose used in other methods. The heat produced by the exothermic reaction is used for other processes of this invention. This higher ratio of alkali metal hydroxide produces a greater yield of carbohydrates from the biomass. The alkali metal hydroxide is recover to be reused in this process.

The carbohydrates produced by this process may be utilized to produce ethanol by fermentation, used as a food for animals and humans or utilized to produce polyols for urethane production. The modified alkali metal lignin, modified lignin, lignin-cellulose resinous products, carbohydrates and hemi-cellulose may be further reacted with organic epoxides, mono- and polysubstituted organic compounds, aldehydes or reacted with amino compounds and/or phenol and aldehydes to produce new and useful products. The lignin-cellulose resinous material or alkali metal lignin-cellulose resinous products may be used as an adhesive such as in producing plywood, in laminates, as filler, etc., and may be further reacted with aldehydes, aminoplasts, phenoplasts, epoxides, ketones, furfuryl alcohol, amines, isocyanates, polyamines, polyisocyanates, mono- and polysubstituted organic compounds such as polyhalides, monohalides organic anhydrides, epihalohydrins, halohydrins and other organic compounds to produce useful resins which may be utilized as adhesives, as laminates as coating agents, as molding agents, as foams. The lignin-cellulose resinous products are soluble in common organic solvents such as ketones, alcohols, glycols, organic esters, etc.

Lignin-cellulose resinous products, modified lignin, carbon dioxide, turpentine, tall oil, carbohydrates and alcohol are produced by reacting the following components:

Component (a): A biomass of lignin-cellulose or cellulose containing plant;
Component (b): An aqueous alkali metal hydroxide;
Component (c): An acidic salt-producing compound;
Component (d): Fermentation agent;
Component (e): Alkaline earth metal oxide or hydroxide;
Component (f): water.

Component (a)

Any suitable biomass consisting of lignin-cellulose or cellulose-containing plant or the products of cellulose-containing plants which contain cellulose may be used in this invention. Many different biomass feedstocks can be used to produce liquid fuels. Some of the common ones are agricultural crops, bioenergy crops, such as fast growing trees, agricultural residues, wood residues and waste streams from municipal solid waste cellulosic fiber fines, baggasse and waste paper. The plant material is preferred to be in the form of small particles such as sawdust, wood chips or ground up biomass. In nature, lignin-cellulose and cellulose are widely distributed. It is found in all plants and they may be used in this process, preferably in a dry, small-particle form. Suitable cellulose-containing plants include, but are not limited to, trees, e-g-, spruce, pine, hemlock, fir, oak, ash, larch, birch, aspen, poplar, cedar, beech, maple, walnut, cypress, redwood, cherry, elm, chestnut, hickory, locust,, sycamore, tulip, tupelo, butternut, apple, alder, magnolia, dogwood, catalpa, boxwood, crabwood, mahogany, greenheart, lancewood, letterwood, mora, prima vera, purple-heart, rosewood, teak, satinwood, mangrove, waffle, orange, lemon, logwood, fustic, osage orange, sappanwood, Brazilwood, barwood, camwood, sandalwood, rubber, gutta, mesquite, and shrubs, e.g., oleander, cypress, junipers, acanthus, pyracantha, ligustrum, lantana, bougainvillea, azalea, feijoa, ilex, fuscia, hibiscus, datura, holly, hydrangea, jasmine, eucalyptus, cottoneaster, xylosma, rhododendron, castor bean,, eugenia, euonymus, fatshedera, aralia, etc.,, and agricultural plants, e.g., cotton, cotton stalks, corn stalks, corn cobs, wheat straw, oat straw, rice straw, cane sugar (bagasse), soybean stalks, peanut plants, pea vines, sugar beet waste, sorghum stalks, tobacco stalks, maize stalks, barley straw, buckwheat straw, quinoa stalks, cassava, potato plants, legume vines and stalks, vegetable inedible portion, etc.,, weeds, grasses,, vines, kelp, flowers and algae. The waste products of agricultural plants which contain cellulose may be ground into small particles and used in this invention. Commercial waste products containing cellulose, e.g., paper, cotton clothes, bagasse wallboard, wood products, etc., may be used in this invention. Cellulose-containing plants which have been partially decomposed, such as grass clippings, humus, peat and certain soft brown coal, may be used in this invention.

Other products of cellulose-containing plants may be recovered in the process of this invention such as waxes, gums,, oils, sugars, wood alcohol, agar, rosin, turpentine, resins, rubber latex,, dyes, glycerol, etc.

Component (b)

Any suitable alkali compound may be used in this invention. Alkali metal compounds are preferred, such as alkali metal oxides, alkali metal hydroxide and mixtures thereof. Mixtures of sodium hydroxide and sodium carbonate may be used. Suitable alkali metal hydroxides include sodium hydroxide, potassium hydroxide and mixtures thereof. Sodium hydroxide or sodium oxide are the preferred alkali metal compounds. The alkali metal hydroxide such as sodium hydroxide is recovered in this process as an aqueous alkali metal solution and reused.

Component (c)

Any suitable salt-forming compound may be used. Acidic salt forming compound that react with the alkali catalyst and then will react with calcium oxide or hydroxide to regenerate the alkali metal oxide or hydroxide is preferred. Suitable salt-forming compounds include carbon dioxide, mineral acids, organic acid, organic acid halides, hydrogen-containing acid salts, e.g., sodium hydrogen sulfate, potassium hydrogen sulfate and, sodium dihydrogen phosphate, sulfur dioxide, sulfurous acid, acid sulfites and mixtures thereof. Carbon dioxide and mineral acids are preferred, especially sulfur oxyacids such as sulfuric acid.

Component (d)

Any suitable method may be used to convert the carbohydrates produced by the process of this invention to produce ethanol. Any suitable yeast which ferments a carbohydrate to produce ethanol may be added to an aqueous solution containing 10% to 40% by weight of carbohydrates produced by the process of this invention, then 5 grams of yeast per 1 to 5 gallons of the aqueous solution of carbohydrates are added. The yeast may be sprinkled on top of the solution at a temperature of 70° F.–80° F. for 12 hours, then stirred in after 12 hours. Stir extremely well and make a lot of bubbles in the mixture. Oxygen from the air helps the yeast grow. The mixture is fermented for up to 2 weeks or until the carbohydrates are used up. The ethanol is then recovered by distillation or by membrane technology. Other method may be use such as using microbial conversion or simultaneous saccharification and fermentation. There are many types of suitable yeast which are commercially available such as PREMIER CUV'EE, MONTRACHET, PASTEUR CHALMMPAGNE, COTE des BLANCS, PASTEUR RED AND LALVIN K1-V-1116 and LALVIN 71 B-1122.

Component (e)

Any suitable alkaline earth metal oxide may be used in this invention that will react with the alkali metal salt used in this process to produce alkali metal oxide or hydroxide. Calcium oxide is the preferred alkaline earth metal oxide.

DETAILED DESCRIPTION OF THE INVENTION

The preferred process to produce carbohydrates from a biomass is to mix about 100 parts by weight of air-dried ground particles of biomass with an aqueous solution containing 20 to 40 parts by weight of a alkali metal hydroxide to wet and distribute the alkali metal hydroxide through out the biomass. The mixture is heated at ambient pressure, elevated pressure or reduced pressure to remove the added water and break the lignin cellulose bond. The heated is continued at a temperature of 140° C. to 220° C. while agitating for about 5–60 minutes or until the reaction becomes exothermic, then heating is stopped and cooling may be necessary. The mixture becomes a bubbling thick fluid mass. The cellulose is converted to carbohydrates by the loss of carbon dioxide and the lignin is modified by the loss of carbon dioxide. The carbon dioxide reacts with some of the alkali metal hydroxide and some escapes. Care has to be taken so that the mixture doesn't become too hot and start burning. A heat exchange system is useful to control the temperature of the mixture and capture the heat for further use in the system. The biomass is converted to a solid mixture containing some un-reacted cellulose, hemi-cellulose, modified alkali metal lignin, carbohydrates, tall oil, turpentine, waxes and other lignin-cellulose resinous products. Most of the biomass is converted to modified lignin and carbohydrates which are water soluble. The free carbon dioxide may be pumped off and stored and used as a salt forming compound.

About 200–500 parts by weight of water is added to the above reacted mixture. Most of the reacted mixture is water soluble, and is filtered or centifuged off the remaining solid biomass. The remaining solid biomass is re-reacted with the next batch of biomass.

The pH of the aqueous solution containing the modified sodium lignin, carbohydrate, lignin-cellulose resinous products and salt is adjusted with a acidic salt forming compound to a pH of 3 to 7. The modified lignin is precipitated. The lignin-cellulose resinous products floats to the top of the aqueous solution and is skimmed off. The modified lignin is separated from the aqueous solution of carbohydrates and salt by filtration, decantation or membrane filtration. Any suitable acidic salt forming compound may be used, but carbon dioxide and/or a sulfur oxyacid, such as sulfuric acid, is preferred. The modified lignin recovered may washed to recover more alkali metal hydroxide or salt if the lignin is to be used for resin production.

This process may be modified wherein the lignin is first removed from the cellulose by breaking the lignin-cellulose bond with the an aqueous alkali catalyst then filtered off of the lignin from the remaining cellulose. The lignin may be burned for heat and to recover some of the alkali metal hydroxide or it may be utilized to produce resinous products or other products such as flame retardant compounds, vanilla, surfactant, phenols, furfural and other extracts.

The aqueous solution of the carbohydrates and salts maybe fermented to produce ethanol. The carbohydrates may also be crystalized out of the solution by evaporating off most of the water, under any suitable method, such as heating under reduced pressure. The carbohydrates may be separated from the salts by the technology of membrane filtration. The carbohydrates are allowed to crystallize out of the aqueous solution, and recovered by filtration or decantation. The aqueous solution still contains soluble carbohydrates and salt, and maybe reconcentrate and more carbohydrates will crystalize out. The lignin-cellulose resins, waxes and tall oil may be skimmed off the top of the solution and terpentine may be distilled off The carbohydrate and salt (NaCl when HCl is used) solution may be evaporated to a concentrated solution or solid, then mixed with cattle feed and used to feed cattle, horses, sheep, goats, rabbits, etc. The carbohydrates may be separated from the salt by crystalizing out the carbohydrates or by membrane technology and used for food. The carbohydrates may also be reacted with organic epoxides to produce polyols which are used in the production of rigid polyurethane foams and resinous products. The solid reacted lignin-cellulose, its aqueous emulsion and the aqueous solution of the carbohydrates may be reacted with polyisocyanates to produce polyurethane foams.

The aqueous carbohydrate and salt solution and/or the carbohydrate crystal in water may be fermented by any suitable means, such as with yeast, to produce ethanol. There are many types of yeast that are used to ferment the carbohydrates of this invention and are commercially available. The carbohydrates may be converted to a more desirable carbohydrate by enzymes. Genetically engineered strains of E. coli maybe used to convert the carbohydrates to ethanol. The ethanol is removed from the aqueous solution by evaporation or by membrane filtration technology.

The aqueous solution containing salt is heated to evaporate the water from the salt by any suitable means or may be separated by using a membrane technology. The water is recovered and reused. The salt is mainly sodium carbonate and sodium-acidic salt forming compound, such as carbonate, sodium acetate or sodium sulfate. An alkaline earth metal oxide such as calcium oxide is added and mixed with the salt in an amount about equal to the mols or greater than the mols of the salt present then reacted to recover the alkali metal hydroxide. Lignin may also be added for fuel and to recover any of the alkali metal hydroxide and turpentine present. The mixture is heated in a recovery furnace until the organic matter is burned then the alkali metal salts are recovered. The aqueous alkali metal salts are reacted with alkaline earth metal oxide to recovery the alkali metal hydroxides.

The object of this invention is to produce carbohydrates, modified lignin, lignin-cellulose resinous products, waxes, turpentine, glycerol, lactic acid and other extracts from lignin-cellulose-containing plant material. Another object is to produce carbohydrates which may be used for food, in the production of ethanol and as the intermediate in the production of other useful organic polymers.

Biomass is converted into useful products such as cellulose, modified lignin, lignin-cellulose resinous products, tall oil, waxes, turpentine, carbohydrates and alcohol by the following steps:

1. Preparation of biomass: Dry biomass is ground into small particles or chips and placed in a digester or heating vessel in the amount of about 100 parts by weight.
2. Adding alkali catalyst: An aqueous solution of an alkali metal hydroxide containing 20 to 40 parts by weight of alkali metal hydroxide is added to the biomass while being agitated.
3. Converting Biomass: The mixture is heated to above the boiling point of water to evaporate off excess water and break the lignin-cellulose bonds, then the heating continues until the mixture is heated to about 140°–200° C. or until the mixture begins to bubble and liquify. The heating is stopped and the reaction is exothermic. The temperature is controlled by an heat exchanger to prevent the biomass from catching on fire. Carbon dioxide is produced in this reaction, some reacts with the sodium hydroxide and some escape. Thereby producing a solid mixture of some cellulose, modified sodium lignin, lignin-cellulose resinous products, hemi-cellulose, tall oil, waxes, turpentine and carbohydrates.
4. Dissolving reacted biomass: About 300–400 parts by weight of water is added to the said solid mixture, agitated and dissolved the water soluble material containing modified sodium lignin, hemi-cellulose, tall oil, waxes, turpentine and carbohydrates. The water soluble material is filtered or decanted from the unsoluble biomass material. The unsoluble biomass is re-washed and water soluble material is filtered off.
5. Adjusting pH: An acidic salt forming compound is added to the aqueous mixture of the water soluble material until the pH is 3–7 or until the lignin is precipitated.
6. Separating components: The organic material that floats to the top is skimmed of. The water soluble carbohydrates and salts are separated by decanting or filtering off the non-water soluble a materials. Fermentation may take place following this step if desired. The carbohydrates may be separated from the salt by membrane technology.
7. Crystalizing carbohydrates: Water is evaporated from the carbohydrates and salt by any suitable means until a concentrated solution is obtained. The carbohydrates crystalize out of the concentrated solution, and the aqueous solution containing the salts is filtered or decanted off the crystals. The aqueous salts are to be reconverted to sodium hydroxide.
8. Fermentation: Water is added to the carbohydrate crystals to form an aqueous solution containing 15–40% carbohydrates. The aqueous solution of carbohydrates are fermented by yeast and ethanol is produced. The ethanol is evaporated from the aqueous solution by any suitable means and the water is re-used. Genetically engineered strains of E-coli may be used to convert the carbohydrates to ethanol.
9. Recovering ethanol: Ethanol is evaporated from the water by any suitable means such as heating under reduced pressure or by membrane technology. The alcohol is dehydrated by azeotropic distillation.
10 Recausticizing: The aqueous salts are heated and most of the water and volatile organic compounds are evaporated off or separated by membrane technology, then it is add to a recovery furnace/boiler along with lignin if desired. The solid or molted salts is dissolved in water and reacted with an alkaline earth metal oxide such as lime. The alkaline earth oxide react with the alkali metal carbonate and alkali metal acid salt to produce alkali metal hydroxide and alkaline earth metal salt which is insoluble. The alkali metal hydroxide is decanted or filtered off and reused in this process.
11. Alkaline earth metal recovery: The insoluble alkaline earth metal is heated in the lime kiln and converted back to alkaline earth metal oxide to be reused in this process. The carbon dioxide may be captures, purified and stored for use in the process.

Fermentation may take place at different steps of this process such as in steps 6 before the salt is removed and in step 8. Membrane filtration may be utilized in a number of different steps of this process. Membrane filtration systems are source selective molecular size or molecular weight.

Molecules of different weight and sizes are stopped and concentrated. Membrane filtration used in the saccharification stage, byproduct recovery stage and fermentation stage to retain enzymes, carbohydrates, salts, yeast and allows water and ethanol to penetrate the membrane. By trapping the yeast, fermentation can proceed continuously at a fraction of the conventional time of 40–50 hours. The membrane filtration technology can be deployed to recover byproducts such as glycerol, lactic acid and others and to reduce the amount of solids going to the evaporator. This technology reduces the cost and increases the revenue.

Evaporation of the water may take place by any suitable means to conserve energy, such as by heating at ambient pressure, increased pressure or lower than ambient pressure or by a multiple-effect evaporators which is preferred. The multiple-effect evaporators remove the bulk of the water by operating in series while at different pressures. Therefore the vapor from one evaporator body can be the steam supply for the next unit. In this approach the original the original feed steam performs the final concentration and the vapor becomes the steam for the next less-concentrated evaporator. Heat can also be supplied to the evaporator from the digester's heat which is recovered by a heat exchange and from the burning of the lignin. The lignin may also be used to heat the recovery boiler and lime kiln.

The recovery boiler is utilized to evaporate the residual moisture from the aqueous salt material and lignin, then burn the organic material to supply heat for steam generation, to recover inorganic chemical in solid or molten form and conditioning the products of combustion for minimal chemical carryover. The solid or molten inorganic salts flows into the dissolving tank to be filtered and recausticizing by the addition of alkaline earth metal oxide such as lime to react with the carbon dioxide radical and acid radical thereby producing sodium hydroxide. The lime mud is precipitate and the aqueous sodium hydroxide is filtered or decanted off and reused. The lime mud is reburned to form CaO and carbon dioxide may be recovered.

From the recovery boiler operation turpentine and tall oils and be obtained. The turpentine is volatile and may be recovered. Tall oil and lignin-cellulose resinous products usually floats to the top of the aqueous salt solution during processing and is skimmed off and processed else where. It is used soaps and paper sizing. The amount of turpentine and tall oil produced depends on the amount of soft wood used especially Southern pine.

DESCRIPTION OF PREFERRED EMBODIMENTS

My invention will be illustrated in detail by the specific examples which follow, it being understood that these preferred embodiments are illustrative of, but not limited to,, procedures which may be used in the production of carbohydrates and ethanol. Parts and percentages are by weight unless otherwise indicated.

EXAMPLE I

About 100 parts by weight of aqueous sodium hydroxide containing 20 part by weight of sodium hydroxide and 100 parts by weight of a dry biomass containing fir sawdust, lawn clippings, weeds, twigs, leaves and pine needles are mixed, then heated to above the boiling point of water at ambient or elevated pressure to remove excess water and break the lignin-cellulose bond, then continue to heat to about 140° to 200° C., while agitating at ambient pressure, with care being taken that the mixture does not burn, for 5 to 60 minutes or until the mixture softens and expands into a dark-brown, bubbling thick paste. It cools to a solid mixture containing a little cellulose and water soluble modified sodium lignin, carbohydrates, lignin-cellulose resinous products, tall oil, turpentine and fatty oils. About 400 parts by weight of water is added to the solid mixture and the water soluble portion dissolves. About 10 parts by weight of cellulose is not dissolved in the water.

Carbon dioxide is added to react with the remaining sodium hydroxide. Then dilute sulfuric acid is added until the pH is 5 to 6.5 while agitating thereby producing some dark-brown lignin-cellulose resinous product which floats to the top, an aqueous solution of carbohydrates, and salt. The lignin is precipitated. The lignin-cellulose resinous product is recovered by skimming it off. The aqueous solution of carbohydrates and salt is recovered by decanting or filtering. The lignin is washed with water to remove any salt, then dried. The lignin-cellulose resinous product and lignin may be molded into useful products by heat and pressure. The aqueous solution of carbohydrates and salts is heated under reduced pressure to concentrate solution. After a few hours the carbohydrates crystalize out. The aqueous solution containing the salt is filtered off and the carbohydrate crystals are recovered.

EXAMPLE 2

Example 1 is modified wherein the carbohydrate crystals are added to 2 gallons of water to make an aqueous solution containing 25% carbohydrates. A yeast, saccharomyces bayanus, in the amount of 3 grams, is add to 40 ml of warm water and remained on top for 15 minutes, then stirred well to suspend the yeast in the water. This yeast was added to the aqueous carbohydrate solution and kept at about 70° F. The solution was stirred daily for 5–6 days or until the hydrometer gives a specific gravity reading of 1.040 then poured into a sterile container with and adapter and an airlock. The gases from the fermentation process escape through the airlock. The solution was left to stand for 1 weeks. The alcohol was distilled off. The alcohol was dehydrated by azeotropic distillation. The carbon dioxide produced may be collected.

EXAMPLE 3

Example 2 was modified wherein the aqueous carbohydrate and salt mixture produced in example 1 is used in place of the aqueous carbohydrate crystals solution.

EXAMPLE 4

Example 1 is modified wherein the carbohydrates are separated from the aqueous salt solution by membrane technology instead of crystalizing the carbohydrates.

EXAMPLE 5

About 100 parts by weight of dry pine sawdust and 100 parts by weight of aqueous sodium hydrate solution containing 25 parts by weight of sodium hydroxide are added to the sawdust while agitating. The mixture is heated to above the boiling point of water until the water has been evaporate and the lignin-cellulose bond has been broken, then the mixture is heated to about 150° C. to 200° C. while agitating. When the mixture starts to expand heating is stopped. The reaction is exothermic, and the mixture continue to expand into a dark-brown, thick liquid paste which solidifies on cooling. Carbon dioxide is produce in the reaction by removing $CO_2$ from the lignin and carbohydrates. The carbon dioxide reacts with sodium hydroxide to form sodium carbonate and some escapes. The solidified mixture contains some cellulose, lignin-cellulose resins, modified lignin, tall oil, turpentine, waxes, but mostly carbohydrates. Water is added to the solidified mixture while agitating and most of the mixture is soluble in water. The aqueous solution is filtered off, then hydrochloric acid is added while agitating until the pH is 5 to 7, thereby producing a lignin-cellulose resinous product, tall oil, waxes and turpentine which floats to the top of the solution and the lignin is precipitated. Carbon dioxide is given off. The lignin-cellulose resinous products, tall oil, waxes and terpentine are skimmed off the top. The aqueous solution is decanted off the lignin. The aqueous solution of carbohydrates and salt is heated under reduced pressure to evaporate off water until the solution is concentrated. The solution is mixed with cattle feed and feed to cattle.

EXAMPLE 6

Example 5 is modified wherein carbohydrates are separated from the aqueous salt solution by means of membrane technology. The aqueous solution of carbohydrates are converted to ethanol by utilizing a yeast by adding about 3 gms yeast to 50 cc of the warm then let it set for 15 minutes then mix well. The yeast mixture is added to the 2 gallons of aqueous carbohydrate solution containing 20–30% carbohydrates then agitated. The solution was stirred daily for 1 week. The carbohydrates were fermented into ethanol. The yeast is selected from the list below:

| | |
|---|---|
| A) Premier Cuv'ee | B) Montrachet |
| C) Pasteur Champage | D) Cote des Blances |
| E) Pasteur Red | F) Lalvin 71 B-1122 |
| G) Lalvin K1-V-1116 | H) Lalvin EC-1118 |

EXAMPLE 7

Example 6 is modified wherein an genetically engineered strain of *E. Coli* was used in place of the yeast to convert the carbohydrates in to ethanol. The ethanol was evaporated from the water under reduced pressure.

EXAMPLE 8

About 20 parts by weight of potassium hydroxide are added to 100 parts by weight of water then 100 parts by weight of white oak sawdust are added while agitating. The mixture is heated while agitating at ambient pressure and up to 140° C. until all the water had evaporated and the lignin-cellulose bond is broken. Heating was continued at 140°–200° C. while agitating or until the mixture began to softens and expands by the loss of carbon dioxide from the cellulose and lignin, then the heating was stopped. The reaction is exothermic and temperature controlled by heat exchange. The thick liquid forms a solid mass when cooled. thereby producing a water-soluble modified sodium lignin, lignin-cellulose resinous products, tall oil, waxes and carbohydrates. About 300 parts by weight of water is mixed and agitated with the solid mass to form an aqueous solution. The aqueous solution is filtered to remove any insoluble cellulose. An aqueous solution of sodium hydrogen sulfate is mixed with the aqueous modified lignin, lignin-cellulose resinous products, waxes and carbohydrates solution until the pH is 5 to 6.5, thereby producing $CO_2$, lignin-cellulose resinous products which floats to the top, carbohydrates and salt solution and modified lignin which precipitates. The lignin-cellulose resinous products are skimmed from the top, then the aqueous solution is filtered off of the modified lignin. The aqueous carbohydrate and salt solution is heated at reduced pressure to evaporate water to concentrate the solution, then the carbohydrates are allowed to crystalized out. The salt water is filtered off to recover the carbohydrates.

EXAMPLE 9

Example 8 is modified when in sawdust from other wood is used in place of white oak and selected from the group consisting of fir, pine, redwood, cedar, oak, spruce, gum, hemlock, walnut, hickory, eucalyptus, birch, poplar, beech, maple, mahogany, aspen, ash, cypress, elm, cherry, sycamore, and mixtures thereof. Other salt-forming compounds is used in place of sodium hydrogen sulfate and selected from the group consisting of dilute sulfuric acid, acetic acid, hydrochloric acid, carbon dioxide, sulfur dioxide, propionic acid, acetic acid chloride, maleic acid, glutaric acid anhydride, oxalic acid, potassium hydrogen sulfide, sodium dihydrogen sulfate and mixtures thereof.

EXAMPLE 10

About 100 parts by weight of an aqueous sodium hydroxide containing 30 parts by weight of sodium hydroxide is mixed with 80 parts by weight of cellulose in the form of cotton. The mixture is heated until the water is evaporated the heated to 150° to 200° C. while agitating at ambient pressure for 5 to 60 minutes or until the cellulose begins to swell and bubble. Heating is stopped. The reaction is exothermic and the heat is controlled by heat exchange. Carbon dioxide is given off. The reacted cellulose cools into a solid mass. 150 parts by weight of water is added and mixed with the solid mass thereby producing an aqueous solution of carbohydrates. Dilute sulfuric acid is added to the aqueous solution while agitating, until the pH is 5 to 6.5. The aqueous solution of carbohydrates and salt is heated under decreased pressure until the solution is concentrated. The carbohydrates are allowed to crystalize out then the salt water is filtered off.

Other cellulose products may be used in place of cotton, such as wood pulp with lignin removed by soda process, wood pulp with lignin removed by the acid process, wood pulp from waste paper and mixtures thereof.

EXAMPLE 11

About 20 parts by weight of sodium hydroxide is dissolved in 80 parts by weight of water and mixed with 100 parts by weight of dry corn cob and stalk particles while agitating. The mixture is heated at ambient pressure to about 140° C. until the water evaporates. Heating is continued at 150° to 200° C. while agitating until the mixture begin to swell and bubble then the heating is stopped. The reaction is exothermic and temperature is controlled by a heat exchanger. Carbon dioxide is given off. When the reaction is complete the mixture cool and forms solid brown particles containing cellulose, hemi-cellulose, modified sodium lignin, lignin-cellulose resinous products and mostly carbohydrates. About 300 parts by weight of water is added to the solid particles and agitated. Most of the solid particles go into solution and is decanted or filtered off the remaining unsoluble particles containing mostly cellulose. The unsoluble particles are re-washed with 50 parts by weight of water and filtered off. The unsoluble particles are re-reacted.

Carbon dioxide is bubble through the aqueous solution to react with any free sodium hydroxide then the pH is adjusted to about 5.5–6 by the addition of acidic acid. Carbon dioxide is given off The lignin-cellulose resinous products floats to the top and are skimmed off. The lignin is precipitated and the aqueous carbohydrate and salt solution is filtered or decanted off the lignin. The salts and carbohydrates are separated by a membrane technology. The aqueous solution containing 20 to 30% carbohydrate was fermented to produce ethanol and carbon dioxide. The ethanol was recovered by membrane technology. Then dehydrated by azeotropic distillation. The carbon dioxide may be collected.

The aqueous solution contain the salts is evaporated, then burned with lignin in a furnace, then dissolved in water. The aqueous solution of sodium carbonate is filtered, then reacted with lime to recover the sodium hydroxide for re-use in the process. The aqueous sodium hydroxide is filtered or decanted from the calcium carbonate. The calcium carbonate is burned in a lime furnace to form calcium oxide for reuse in the process. The water is filtered and reused.

Other dry cellulose-containing plant particles may be used in place of corn cobs, such as corn stalks, seaweed, cotton stalks, rice straw, wheat straw, oat straw, barley straw, soybean stalks, cane sugar stalks, pea vines, bean vines, sugar beet waste, sorghum stalks, tobacco stalks, maize stalks, buck-wheat straw, weeds, bushes,, grass, algae, humus, peat and mixtures thereof.

EXAMPLE 12

Example 8 is modified wherein 10 parts by weight of the reacted biomass consisting of modified alkali lignin, lignin-cellulose resinous products, carbohydrate, tall oil and sodium carbonate is mixed and reacted with 5 parts by weight of epichlorohydrin thereby producing an polyepoxy resin. Other epihalohydrin compounds may be used in place of epichlorohydrin such as, epifluorohydrin and epibromohydrin

EXAMPLE 13

Example 1 is modified wherein 10 parts by weight of the aqueous modified sodium lignin, lignin-cellulose resinous products, carbohydrates and sodium carbonate, containing 50% water, 0.1 part by weight of silicone surfactant and 15 parts by weight of polymeric MDI are added and mixed, the mixture expands, hardens and produces a rigid polyurethane foam.

EXAMPLE 14

Example 1 is modified wherein 10 parts by weight of the carbohydrate crystals, 2 parts by weight of water, 0.5 part by weight of phosphoric acid and 5 parts by weight propylene oxide are mixed and reacted thereby producing a polyol.

EXAMPLE 15

Example 1 is modified wherein the aqueous solution of modified sodium lignin, lignin-cellulose resinous products, carbohydrates and semi-cellulose is reacted with an organic compounds to produce resinous products. The organic compounds are selected from aldehydes, mono-or poly halogenated organic compounds, isocyanates, polyisocyanates, amino compounds, amines, polyamines, polyamines epoxides, polyepoxides, epichlorohydrins, aminoplasts, phenoplasts and mixtures thereof.

Although specific materials and conditions were set forth in the above examples, these were merely illustrative of preferred embodiments of my invention. Various other compositions, such as the typical materials listed above, may be used where suitable. The reactive mixtures and products of my invention may have other agents added thereto in order to enhance or otherwise modify the reaction and products. Other modifications of my invention will occur to those skilled in the art upon reading my disclosure. These are intended to be included within the scope of my invention, as defined in the appended claims.

I claim:

1. The process for production of the compounds, lignin, lignin-cellulose resinous compounds, carbon dioxide, and carbohydrates produced from biomass by the process consisting of mixing, heating, and reacting die components by the following steps:

(1) preparation of biomass:
      excess water is removed from the biomass and ground or chipped into small pieces and utilized in the amount of 100 parts by weight;

(2) adding aqueous alkali metal hydroxide:
      aqueous solution of alkali metal hydroxide containing 25 to 50 parts by weight of alkali metal hydroxide is added and mixed with the biomass;

(3) converting biomass:
      the biomass is heated to about 140° C. to evaporate the water and break the Lignin-cellulose bond then heating is continued while agitating and the biomass becomes a thick paste;

(4) dissolving converted biomass:
      water in the amount of 200 to 400 parts by weight is added and mixed with the convened biomass thereby dissolving most of the converted biomass, then filtered or decanted off the non-water soluble biomass;

(5) adjusting the pH:
      an acidic salt forming compound, carbon dioxide, is added to the aqueous converted biomass solution until the pH is 3–7;

(6) separating the components:
      the lignin-cellulose resinous products are skimmed from the top of the aqueous solution then the aqueous solution containing the carbohydrates and salt is filtered or decanted off the precipitated lignin;

(7) crystalizing carbohydrates:
      the aqueous carbohydrates and salt solution is heated to evaporate water to concentrate the solution, then the carbohydrates are precipitated out, and the aqueous salt solution is filtered or decanted off;

(8) recausticing:
      the aqueous solution containing salts is heated to evaporate excess water then placed in a furnace, with or without lignin, burned to remove organic material, then added to water, filtered, then reacted with an alkaline earth metal oxide, to produce alkali metal hydroxide for reuse and alkaline earth metal salt which precipitates;

(9) alkaline earth metal oxide recovery:
      the alkaline earth metal salt is heated in a lime kiln to produce alkaline earth metal oxide and carbon dioxide fur reuse.

2. The process of claim 1 wherein the alkali metal hydroxide is sodium hydroxide.

3. A process for the production of carbohydrates from biomass that does not contain lignin by the process consisting of mixing, heating and reacting by the following steps:

(1) biomass is ground into small particles;
   (2) aqueous sodium hydroxide is added to and mixed with the biomass;

(3) biomass is heated to about 140 degrees C. to remove excess water;

(4) biomass is heated to 140 to 200 degree C. until the biomass become a thick paste;

(5) water is added and mixed to form an aqueous solution, then filtered to remove non-soluble materials;

(6) carbon dioxide is added and mixed with the aqueous solution to react the sodium hydroxide to form sodium carbonate;

(6) the aqueous solution is concentrated by evaporating off water then the carbohydrates form crystals and the aqueous solution is filtered or decanted off thereby recovering the carbohydrates;

(7) lime oxide is added and reacted with the aqueous solution of sodium carbonate to form sodium hydroxide and calcium carbonate which precipitates, and the aqueous sodium hydroxide is decanted off to be reused;

(8) calcium carbonate is heated in a lime kiln to recover calcium oxide for reuse and the carbon dioxide is collected for reuse.

* * * * *